United States Patent [19]

Meli et al.

[11] Patent Number: 5,011,833
[45] Date of Patent: Apr. 30, 1991

[54] NOVEL DERIVATIVES OF 6,11-DIHYDRO-DIBENZO(C,F)(1,2,5)-THIADIAZEPINE 5,5-DIOXIDE, SALTS THEREOF AND APPROPRIATE PROCESSES FOR THE PREPARATION THEREOF

[75] Inventors: Franco Borsini, Alberto Meli, Giovanna Volterra, Firenze; Danilo Giannotti, Lucca; Vittorio Pestellini, Firenze, all of Italy

[73] Assignee: A. Menarini Industrie Farmaceutiche Riunite, Florence, Italy

[21] Appl. No.: 393,517

[22] Filed: Aug. 11, 1989

[30] Foreign Application Priority Data

Aug. 12, 1988 [IT] Italy ................................ 9466 A/88

[51] Int. Cl.$^5$ ..................... C07D 285/36; A61K 31/55
[52] U.S. Cl. ..................................... 511/211; 540/545
[58] Field of Search .......................... 540/545; 514/211

[56] References Cited

U.S. PATENT DOCUMENTS

| 3,254,631 | 6/1966 | Yale | 540/550 |
| 3,268,557 | 8/1966 | Weber | 540/545 |
| 4,659,707 | 4/1987 | Giano | 540/495 |

FOREIGN PATENT DOCUMENTS 3235795 3/1984 Fed. Rep. of Germany ...... 540/495

Primary Examiner—Robert Gerstl
Attorney, Agent, or Firm—McGlew & Tuttle

[57] ABSTRACT

Novel derivatives of 11-carbonyl-6,11-dihydrodibenzo[c,f][1,2,5]thiadiazepine 5,5-dioxide of the general formula

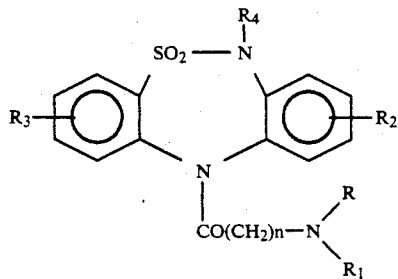

wherein
R and $R_1$, which can be different, represent a hydrogen atom or a ($C_1$-$C_5$) alkyl or ($C_1$-$C_4$)hydroxyalkyl group, or R and $R_1$ together can form a 5-membered and/or 6-membered heterocyclic ring which may contain a further heteroatom,
$R_2$ and $R_3$, which can be different, represent a hydrogen atom, a ($C_1$-$C_3$)alkoxy, ($C_1$-$C_3$)alkyl, nitro, amino or ($C_1$-$C_3$)alkylamino, halogen, halogeno-alkyl or hydroxyl group,
$R_4$ represents a hydrogen atom or a ($C_1$-$C_4$) alkyl, alkylaryl or ($C_1$-$C_6$)alkylamino group, and
n assumes values of 0, 1 or 2, and
non-toxic, pharmaceutically acceptable salts thereof, obtained by addition of acids or alkyl halides.

9 Claims, No Drawings

NOVEL DERIVATIVES OF 6,11-DIHYDRO-DIBENZO(C,F)(1,2,5)-THIADIAZEPINE 5,5-DIOXIDE, SALTS THEREOF AND APPROPRIATE PROCESSES FOR THE PREPARATION THEREOF

DESCRIPTION

The invention relates to novel derivatives of 6,11-dihydro-dibenzo[c,f][1,2,5]thiadiazepine 5,5-dioxide, to salts thereof, to pharmaceutical preparations containing these products and to methods for producing and using these derivatives.

Derivatives of 6,11-dihydro-dibenzo[c,f][1,2,5]-thiadiazepine 5,5-dioxide are already known in the literature. More in detail, U.S. Pat. Nos. 3,222,789 and 3,274,058 describe monoalkylaminoalkyl and dialkylaminoalkyl derivatives of 6,11-dihydro-dibenzo[c,f][1,2,5]-thiadiazepine 5,5-dioxide, corresponding to the structure:

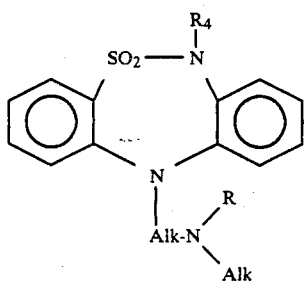

where R can be hydrogen or another alkyl group.

According to the two U.S. patents, the abovementioned compounds should be useful as psychotropic agents and as muscle relaxation agents. It is, however, known that toxicity studies have shown that such compounds can, even in sub-toxic doses, induce unpleasant side effects upon the cardiovascular system in experimental animals (A. Weber, J. Frossard, Ann. Pharm. Franc. 24, 1966, No. 6, 445–450). Such secondary effects therefore constitute an important limitation to the use of an antidepressant drug which normally must be administered over long periods of time.

It has now been found that the introduction of a carbonyl group

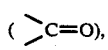

to separate the nitrogen atom in the 11-position from the alkylaminoalkyl chain in the structure of 6,11-dihydro-dibenzo[c,f][1,2,5]thiadiazepine 5,5-dioxide, leads to a clear reduction in the side effects typical of this structure.

The present invention therefore relates to novel 11-carbonyl derivatives of dibenzothiadiazepine, of the general formula I:

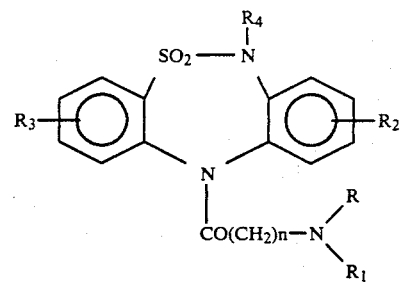

wherein

R and $R_1$, which can be different, represent a hydrogen atom or a $(C_1-C_5)$alkyl or $(C_1-C_4)$-hydroxyalkyl group, or R and $R_1$ together can form a 5-membered and 6-membered heterocyclic ring which may have a further heteroatom, $R_2$ and $R_3$, which can be different, represent a hydrogen atom, a $(C_1-C_3)$alkoxy, $(C_1-C_3)$alkyl, nitro, amino or $(C_1-C_3)$alkylamino, halogen, halogenoalkyl or hydroxyl group, $R_4$ represents a hydrogen atom or a $(C_1-C_4)$alkyl, alkylaryl or $(C_1-C_6)$alkylamino group, and n assumes values of 0, 1 or 2.

The compounds constituting the subject of the present patent application exhibit a psychotropic action equal to, and in some cases even greater than, that possessed by the compounds described in U.S. Pat. Nos. 3,274,058 and 3,322,789; in comparison with these latter, they have, however, the advantage of a lower incidence of side effects, and in particular are free of preconvulsive effects and do not alter the blood pressure.

The structural characteristic, which distinguishes the compounds of the present invention from analogs already known, resides in the presence of a keto group which separates the nitrogen atom in the 11-position from the alkyl substituent; in this way, the basic nitrogen becomes an amide nitrogen.

Compounds of this invention of particular interest are those in which $R_2$ and $R_3$ are hydrogen, $R_4$ is methyl, n assumes values of 1 or 2, and R and $R_1$ are hydrogen, methyl or ethyl.

The preferred compound of this invention is 6-methyl-6,11-dihydro-11-(N,N-dimethylaminoacetyl)-dibenzo[c,f][1,2,5]thiadiazepine 5,5-dioxide.

The starting materials used for the preparation of the derivatives of the general formula I are, according to the method of the present invention, the corresponding 6,11-dihydro-dibenzo[c,f][1,2,5]thiadiazepine 5,5-dioxides of the general formula II

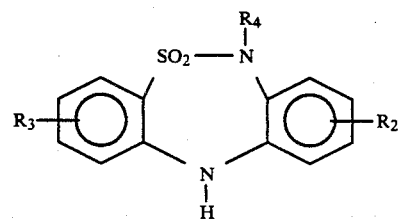

where the substituents $R_2$, $R_3$ and $R_4$ assume the meanings already defined for the compounds of the general formula I.

The method of the present invention comprises treating the compounds of the general formula II with the appropriate ω-halogenoacyloyl halide to obtain the corresponding 6,11-dihydro-11-(ω-halogenaoalkyl)-dibenzo[c,f][1,2,5]thiadiazepine 5,5-dioxides of the general formula III

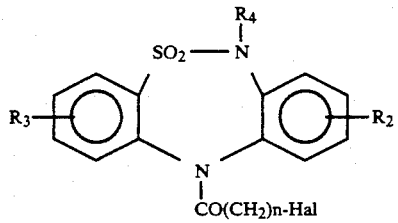

where $R_2$, $R_3$ and $R_4$ have the meaning already defined for the compounds of the general formula I, Hal stands for halogen and n assumes values of 1 or 2. The reaction is carried out in an organic solvent or in an excess of halogenoacyloyl halide, and with heating.

The compounds of the general formula III are not always purified, since they are sometimes used in the crude state. By treatment with the appropriate amine, or with ammonia or heterocyclic compound, such compounds either in the pure or crude form give the corresponding compounds of the general formula I; this reaction is preferably carried out in a polar solvent such as, for example, acetone, dioxane or alcohols at ambient temperature or under reflux.

Alternatively, the compounds of the general formula I, in which n=1 or 2, can be obtained by reacting 6,11-dihydro-dibenzo[c,f][1,2,5]thiadiazepine 5,5-dioxide with a suitable acid in an activated form such as, for example, an active ester or anhydride or chlorides, of the general formula:

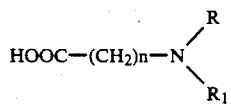

where R and $R_1$ have the ready meaning al defined for the compounds of the general formula I and n assumes values of 1 and 2. Such a reaction is preferably carried out in an organic solvent, or in an excess of the acid, with heating.

The compounds of the general formula I, if n=0, are obtained by treating 6,11-dihydro-dibenzo[c,f][1,2,5]-thiadiazepine 5,5-dioxide with a derivative of carbonic acid such as, for example, trichloromethyl chloroformate or carbonyl chloride, and subsequent reaction of the intermediate obtained with ammonia or a substituted amine; the reaction is preferably carried out by treating the sodium salt of the compound of the general formula II.

EXAMPLE 1

Preparation of 6-6,11-dihydro-11-chloroacetyldibenzo[c,f][1,2,5]-thiadiazepine 5,5-dioxide 15 g (0.057 mol) of 6-methyl-6,11-dihydrodibenzo[c,f][1,2,5]thiadiazepine 5,5-dioxide in 100 ml of chloroacetyl chloride are kept for 2 hours under reflux. The mixture is poured into water and ice with stirring, and the oil which separates out solidifies. The solid is filtered off, washed with water and dried.

Crystallized from ethyl acetate: melting point 141°–3° C., quantity obtained 15.3 g, yield 80%.

In an analogous manner, other intermediates the general formula III are prepared, in particular the following:

6-Methyl-6,11-dihydro-11-(3-chloropropionyl)dibenzo[c,f][1,2,5]thiadiazepine 5,5-dioxide, melting point 131°–132° C.

2-Chloro-3,6-dimethyl 6,11-dihydro-11-chloroacetyl-dibenzo[c,f][1,2,5]thiadiazepine 5,5-dioxide, melting point 164°–6° C. 6-Ethyl-6,11-dihydro-11-chloroacetyl-dibenzo[c,f][1,2,5]thiadiazepine 5,5-dioxide, melting point 174°–176° C.

2-Chloro-6-methyl-6,11-dihydro-11-chloroacetyl-dibenzo[c,f][1,2,5]thiadiazepine 5,5-dioxide, melting point 183°–184° C.

6-Methyl-2-methoxy-6,11-dihydro-11-chloroacetyl-dibenzo[c,f][1,2,5]thiadiazepine 5,5-dioxide, melting point 178°–9° C.

6-Propyl-6,11-dihydro-11-chloroacetyl-dibenzo[c,f][1,2,5]thiadiazepine 5,5-dioxide, melting point 147°–48° C.

2-Trifluoromethyl-6-methyl-6,11-dihydro-11-chloroacetyldibenzo[c,f][1,2,5]thiadiazepine 5,5-dioxide, melting point 121°–122° C.

9-Chloro-6-methyl-6,11-dihydro-11-chloroacetyl-dibenzo[c,f][1,2,5]thiadiazepine 5,5-dioxide: melting point 202°–203° C.

6,9-Dimethyl-6,11-dihydro-11-chloroacetyl-dibenzo[c,f][1,2,5]thiadiazepine 5,5-dioxide: melting point 155°–157° C.

8-Chloro-6-methyl-6,11-dihydro-11-chloroacetyl-dibenzo[c,f][1,2,5]thiadiazepine 5,5-dioxide: melting point 158°–159° C.

3-Chloro-6-methyl-6,11-dihydro-11-chloroacetyl-dibenzo[c,f][1,2,5]thiadiazepine 5,5-dioxide: melting point 209°–210° C.

EXAMPLE 2

6-Methyl-6,11-dihydro-11-[3-(N,N-dimethylamino)propionyl]dibenzo[c,f][1,2,5]thiadiazepine 5,5-dioxide hydrochloride 5.5 g (0.037 mol) of sodium iodide are added to 13 g (0.037 mol) of 6-methyl-6,11-dihydro-11-(3-chloropropionyl)-dibenzo[c,f][1,2,5]thiadiazepine 5,5-dioxide in 100 ml of acetone, and the mixture is heated under reflux for 30 minutes. After cooling, 7 ml of aqueous 33% dimethylamine are added, and the mixture is kept with stirring at ambient temperature for 16 hours. It is concentrated and the residue is treated with 5% HCl, the insoluble fraction is filtered off and the filtrate is alkalized with $NaHCO_3$; a solid forms, which is filtered off, washed with water and dried.

Crystallized from 95° ethanol, melting point 189°–90° C., quantity obtained 10 g, yield 68%.

EXAMPLE 3

6-Methyl-6,11-dihydro-11-carbamoyl-dibenzo[c,f][1,2,5]thiadiazepine 5,5-dioxide 0.9 g (0.027 mol) of 80% sodium hydride are added to 7 g (0.027 mol) of 6-methyl-6,11-dihydro-dibenzo[c,f][1,2,5]thiadiazepine 5,5-dioxide in 200 ml of dioxane, and the mixture is heated for 30 minutes at 80° C. After cooling, 5.4 g of trichloromethyl chloroformate are added dropwise, with cooling in an ice bath, and the mixture is left to stand overnight. Gaseous $NH_3$ is then introduced up to saturation, the mixture is filtered, and the filtrate is concentrated and diluted with water. This gives a solid which is filtered, washed and dried.

Crystallized from ethanol, melting point 240°-2° C., quantity obtained 4.9 g, yield 60%.

EXAMPLE 4

Proceeding as described for the two preceding compounds, the following further compounds of the general formula I are prepared, which are reported here with their respective melting points:

1. 6-Methyl-6,11-dihydro-11-[(4-methyl-piperazin-1-yl)acetyl]-dibenzo[c,f][1,2,5]thiadiazepine 5,5-dioxide: melting point 143°-44° C., obtained according to Example 2 from 6-methyl-6,11-dihydro-11-chloroacetyl-dibenzo[c,f][1,2,5]thiadiazepine 5,5-dioxide.

2. 6-Methyl-6,11-dihydro-11-{[4-(2-hydroxyethyl)piperazin-1-yl]-acetyl}-dibenzo[c,f][1,2,5]thiadiazepine 5,5-dioxide dihydrochloride: melting point 236°-38° C., obtained according to Example 2 from 6-methyl-6,11-dihydro-11-chloroacetyl-dibenzo[c,f][1,2,5]-thiadiazepine 5,5-dioxide.

3. 6-Methyl-6,11-dihydro-11-(N,N-dimethylaminoacetyl)dibenzo[c,f][1,2,5]thiadiazepine 5,5-dioxide: melting point 179°-181° C., hydrochloride n H$_2$O: m.p. 198° C. dec. (isopropanol/H$_2$O), obtained according to Example 2 from 6-methyl-6,11-dihydro-11-chloroacetyl-dibenzo[c,f][1,2,5]thiadiazepine 5,5-dioxide.

4. 2-Chloro-3,6-dimethyl-6,11-dihydro-11-[(4-methyl-piperazin-1-yl)-acetyl]-dibenzo [c,f][1,2,5]thiadiazepine 5,5-dioxide: melting point 156°-58° C., obtained according to Example 2 from 2-chloro-3,6-dimethyl-6,11-dihydro-11-chloroacetyl-dibenzo[c,f][1,2,5]-thiadiazepine 5,5-dioxide.

5. 2-Chloro-3,6-dimethyl-6,11-dihydro-11-[(4-phenyl-piperazin-1-yl)-acetyl]-dibenzo [c,f][1,2,5]thiadiazepine 5,5-dioxide: melting point 194°-96° C. obtained according to Example 2 from 2-chloro-3,6-dimethyl-6,11-dihydro-11-chloroacetyl-dibenzo[c,f][1,2,5]-thiadiazepine 5,5-dioxide.

6. 2-Chloro-3,6-dimethyl-6,11-dihydro-11-{[4-(2-hydroxyethyl)-piperazin-1-yl]-acetyl}-dibenzo[c,f][1,2,5]thiadiazepine 5,5-dioxide dihydrochloride: melting point 234°-36° C., obtained according to Example 2 from 2-chloro-3,6-dimethyl-6,11-dihydro-11-chloroacetyl-dibenzo[c,f][1,2,5]thiadiazepine 5,5-dioxide.

7. 2-Chloro-3,6-dimethyl-6,11-dihydro-11-{[4-(pyrimidin-2-yl)-piperazin-1-yl]-acetyl}-dibenzo[c,f][1,2,5]-thiadiazepine 5,5-dioxide: melting point 180°-82° C., obtained according to Example 2 from 2-chloro-3,6-dimethyl-6,11-dihydro-11-chloroacetyl-dibenzo[c,f][1,2,5]thiadiazepine 5,5-dioxide.

8. 2-Chloro-3,6-dimethyl-6,11-dihydro-11-(N-isopropylamino-acetyl)-dibenzo[c,f][1,2,5]thiadiazepine 5,5-dioxide hydrochloride: melting point 248°-50° C., obtained according to Example 2 from 2-chloro-3,6-dimethyl-6,11-dihydro-11-chloroacetyl-dibenzo[c,f][1,2,5]thiadiazepine 5,5-dioxide.

9. 2-Chloro-3,6-dimethyl-6,11-dihydro-11-(N,N-dimethylamino-acetyl)-dibenzo[c,f][1,2,5]thiadiazepine 5,5-dioxide hydrochloride: melting point 240°-42° C., obtained according to Example 2 from 2-chloro-3,6-dimethyl-6,11-dihydro-11-chloroacetyl-dibenzo[c,f][1,2,5]thiadiazepine 5,5-dioxide.

10. 2-Methoxy-6-methyl-6,11-dihydro-11-[N,N-dimethylamino-acetyl)-dibenzo[c,f][1,2,5]thiadiazepine 5,5dioxide hydrochloride: melting point 270°-72°, obtained according to Example 2 from 2-methoxy-6methyl-6,11-dihdyro-11-chloroacetyl-dibenzo[c,f][1,2,5]thiadiazepine 5,5-dioxide.

11. 6-Methyl-6,11-dihdyro-11-(N,N-dimethylcarbonyl)-dibenzo[c,f][1,2,5]thiadiazepine 5,5-dioxide: melting point 170°-71° C., obtained according to Example 3 from 6-methyl-6,11-dihydro-dibenzo[c,f][1,2,5]-thiadiazepine 5,5-dioxide.

12. 6-Ethyl-6,11-dihydro-11-(N,N-dimethylaminoacetyl)dibenzo[c,f][1,2,5]thiadiazepine 5,5-dioxide: melting point 115°-116° C., obtained according to Example 2 from 6-ethyl-6,11-dihydro-11-chloroacetyldibenzo[c,f][1,2,5]thiadiazepine 5,5-dioxide.

13. 6-Methyl-6,11-dihydro-11-(N,N-diethylaminoacetyl)dibenzo[c,f][1,2,5]thiadiazepine 5,5-dioxide: melting point 161°-62° C., obtained according to Example 2 from 6-methyl-6,11-dihydro-11-chloroacetyl-dibenzo[c,f][1,2,5]thiadiazepine 5,5-dioxide.

14. 6-Methyl-6,11-dihydro-11-(N-isopropylaminoacetyl)dibenzo[c,f][1,2,5]thiadiazepine 5,5-dioxide: melting point 115°-17° C., obtained according to Example 2 from 6-methyl-6,11-dihydro-11-chloroacetyl-dibenzo[c,f][1,2,5]thiadiazepine 5,5-dioxide.

15. 6-Methyl-6,11-dihydro-11-(N-t-butylamino-acetyl)-dibenzo[c,f][1,2,5]thiadiazepine 5,5-dioxide: melting point 143°-45° C., obtained according to Example 2 from 6-methyl-6,11-dihydro-11-chloroacetyl-dibenzo[c,f][1,2,5]thiadiazepine 5,5-dioxide.

16. 6-Methyl-6,11-dihydro-11-[(morpholin-1-yl)-acetyl]dibenzo[c,f][1,2,5]thiadiazepine 5,5-dioxide: melting point 129°-31° C., obtained according to Example 2 from 6-methyl-6,11-dihydro-11-chloroacetyl-dibenzo[c,f][1,2,5]thiadiazepine 5,5-dioxide.

17. 6-Methyl-6,11-dihydro-11-[(4-methylpiperidin-1-yl)acetyl]-dibenzo[c,f][1,2,5]thiadiazepine 5,5-dioxide: melting point 159°-60° C., obtained according to Example 2 from 6-methyl-6,11-dihydro-11-chloroacetyl-dibenzo[c,f][1,2,5]thiadiazepine 5,5-dioxide.

18. 6-Methyl-6,11-dihydro-11-[(pyrrolidin-1-yl)-acetyl]-dibenzo[c,f][1,2,5]thiadiazepine 5,5-dioxide: melting point 175°-77° C., obtained according to Example 2 from 6-methyl-6,11-dihydro-11-chloroacetyl-dibenzo[c,f][1,2,5]thiadiazepine 5,5-dioxide.

19. 6-Methyl-6,11-dihydro-11- (N-methylamino-acetyl)-dibenzo[c,f][1,2,5]thiadiazepine 5,5-dioxide: melting point 135°-37° C., obtained according to Example 2 from 6-methyl-6,11-dihydro-11-chloroacetyl-dibenzo[c,f][1,2,5]thiadiazepine 5,5-dioxide.

20. 2-Chloro-6-methyl-6,11-dihydro-11-(N,N-dimethylamino-acetyl)-dibenzo[c,f][1,2,5]thiadiazepine 5,5dioxide: melting point 138°-39° C., obtained according to Example 2 from 2-chloro-6-methyl-6,11-dihydro-11-chloroacetyl-dibenzo[c,f][1,2,5]thiadiazepine 5,5dioxide.

21. 6-Propyl-6,11-dihydro-11-(N,N-dimethylaminoacetyl)dibenzo[c,f][1,2,5]thiadiazepine 5,5-dioxide hydrochloride: melting point 147°-149° C., obtained according to Example 2 from 6-propyl-6,11-dihydro-11-chloroacetyl-dibenzo[c,f][1,2,5]thiadiazepine 5,5dioxide.

22. 9-Chloro-6-methyl-6,11-dihydro-11-(N,N-dimethylamino-acetyl)-dibenzo[c,f][1,2,5]thiadiazepine 5,5dioxide: melting point 175°-176° C., obtained according to Example 2 from 9-chloro-6-methyl-6,11-dihydro-11-chloroacetyl-dibenzo[c,f][1,2,5]thiadiazepine 5,5-dioxide.

23. 6,9-dimethyl-6,11-dihydro-11-(N,N-dimethylaminoacetyl)-dibenzo[c,f][1,2,5]thiadiazepine 5,5-dioxide: melting point 135°-137° C., obtained according to Example 2 from 6,9-dimethyl-6,11-dihydro-11-chloroacetyl-dibenzo[c,f][1,2,5thiadiazepine 5,5-dioxide.

24. 8-chloro-6-methyl-6,11-dihydro-11-(N,N-dimethylamino-acetyl)-dibenzo[c,f][1,2,5]thiadiazepine 5,5-dioxide: melting point 132°-133° C., obtained according to Example 2 from 8-chloro-6-methyl-6,11-dihydro-11-chloroacetyl-dibenzo[c,f][1,2,5]thiadiazepine 5,5-dioxide.

25. 3-chloro-6-methyl-6,11-dihydro-11-(N,N-dimethylaminoacetil)dibenzo[c,f][1,2,5]thiadiazepine 5,5-dioxide hydrochloride: melting point 163°-165° C. dec., obtained according to Example 2 from 3-chloro-6-methyl-6,11-dihydro-11-chloroacetyl-dibenzo[c,f][1,2,5]thiadiazepine 5,5-dioxide.

26. 2-trifluoromethyl-6-methyl-6,11-dihydro-11-(N,N-dimethylamino-acetyl)dibenzo[c,f][1,2,5]thiadiazepine 5,5-dioxide: melting point 156°-157° C., obtained according to Example 2 from 2-trifluoromethyl-6-methyl-6,11-dihydro-11-chloroacetyl-dibenzo[c,f][1,2,5]thiadiazepine 5,5-dioxide.

The pharmacological evaluation was carried out by means of various tests which predict the psychotropic activity, in particular that of the antidepressant type (Willner, 1984, Psychopharmacology 83:1). The compounds of the present patent are active, for example in the "apomorphine test" (Puech et al., 1981, Psychopharmacology 75:84). In particular, 6-methyl-6,11-dihydro-11- N,N-dimethylamino-acetyl)dibenzo[c,f][1,2,5]thiadiazepine 5,5-dioxide has the following pharmaceutical characteristics: (a) ED-50 in counteracting the hypothermia induced by apomorphine (Puech et al., 1981, Psychopharmacology 75:84) in mice=13.5 mg/kg by the oral route and 4.7 mg/kg by the intraperitoneal route; (b) minimum oral dose effective in counteracting reserpine hypothermia (Bourin et al., 1983, Arzneim-Forsch/Drug Res 33:1173) in mice=25 mg/kg; (c) oral LD-50 in mice 1920 mg/kg; (d) does not induce convulsions; (e) does not alter the motor activity; (f) does not alter the blood pressure; (g) induces very weak anticholinergic effects; (h) is not cardiotoxic; (i) reduces duodenal ulcers.

Table 1 summarizes the test results.

Under the same experimental conditions used by us, 6-methyl-11-(3-dimethylaminopropyl)-6,11-dihydrodibenzo[c,f][1,2,5]thiadiazepine 5,5-dioxide (one of the most interesting compounds from U.S. Pat. No. 3,274,058) shows the following pharmacological characteristics: (a) minimum oral dose effective in counteracting reserpine hypothermia in mice=100 mg/kg; (b) oral LD-50 in mice=655 mg/kg; (c) induces convulsions; (d) increases the motor activity; (e) increases the blood pressure; (f) possesses anticholinergic effect.

The compounds to which the present application refers are suitable for either oral or parenteral or suppositorial administration in the form of: tablets, capsules, powders, granules, syrups, gel spray, lotions, suspensions, injectable solutions and suppositories.

The pharmaceutical formulations suitable for administration contain the compounds, which are the subject of the invention, in a quantity of between 0.1 and 30%, preferably between 0.5 and 10% by weight, in a mixture with the usual excipients such as, for example: gelling agents, suppository bases, auxiliaries for tablets and other excipients for the active ingredients such as, for example, antioxidants, dispersants, emulsifiers, antifoams, flavor improvers, preservatives, solubilizers and colorants.

It is advisable to administer the active compound in one or more daily doses of between 0.1 and 50 mg/kg body weight, preferably between 0.5 and 20 mg/kg body weight.

The optimum doses and the administration route of the active compounds, required in any particular case, are easily determined by any person skilled in the art in accordance with his experience.

The present invention also comprises pharmaceutical formulations which represent combinations of one or more compounds, which are the subject of the invention, as pure formulations representing combinations of one or more compounds, subject of the invention, and one or more compounds which are pharmaceutically active towards the central nervous system.

TABLE 1

| Compound | Hypothermia inhibition (*) from Apo16: ED-50 | LD-50 (mg/kg/os) (**) |
|---|---|---|
| 1 | ++ | 1500-2000 |
| 2 | ++ | 750-1000 |
| 3 | + | greater than 2000 |
| 4 | + | 500-700 |
| 5 | + | 1000-1500 |
| 6 | ++ | 1500-2000 |
| imipramine | ++ | less than 350 |

(*) Apomorphine 16 mg/kg (Apo16) was administered to Swiss male mice by the subcutaneous route 30 minutes before measuring the rectal temperature. The compounds were administered by the oral route 60 minutes before measuring the rectal temperature.
ED-50 = dose of compound which reduces by 50% the hypothermia caused by Apomorphine administered at 16 mg/kg by the subcutaneous route:
++ = ED-50 comprised in the range of 4-15 mg/kg/os
+ = ED-50 comprised in the range of 15-25 mg/kg/os
(**) LD-50 = dose of compound which causes the death of 50% of the mice (Swiss male mice) after 14 days.
Compounds:
1. 6-methyl-6,11-dihydro-11-(N,N-dimethylamino-acetyl)dibenzo c,f 1,2,5 thiadiazepine 5,5-dioxide
2. 6-methyl-6,11-dihydro-11-(N-methylamino-acetyl)dibenzo c,f 1,2,5 thiadiazepine 5,5-dioxide
3. 6-methyl-6,11-dihydro-11-(N,N-diethylamino-acetyl)dibenzo c,f 1,2,5 thiadiazepine 5,5-dioxide
4. 6-methyl-6,11-dihydro-11-3-(N,N-dimethylamino)propionyl dibenzo c,f 1,2,5 thiadiazepine 5,5-dioxide
5. 8-chloro-6-methyl-6,11-dihydro-11-(N,N-dimethylamino-acetyl)dibenzo c,f 1,2,5 thiadiazepine 5,5-dioxide
6. 6,9-dimethyl-6,11-dihydro-11-(N,N-dimethylamino-acetyl)dibenzo c,f 1,2,5 thiadiazepine 5,5-dioxide

We claim:

1. A novel derivative of 11-carbonyl-6,11-dihydrodibenzo[c,f][1,2,5]thiadiazepine 5,5-dioxide of the general formula

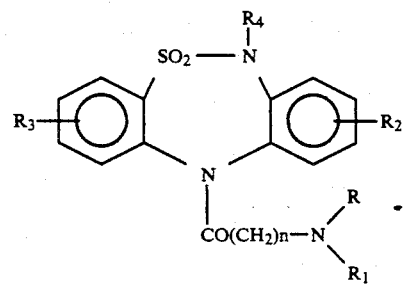

wherein
R and $R_1$, which can be different, represent a hydrogen atom or a $(C_1-C_5)$alkyl or $(C_1-C_4)$hydroxyalkyl group, or R and $R_1$ together can form a 5-membered and/or 6-membered heterocyclic ring which may contain a further heteroatom, $R_2$ and $R_3$, which can be different, represent a hydrogen atom, a ($C_1$–$C_3$)alkoxy, ($C_1$–$C_3$)alkyl, nitro, amino or ($C_1$–$C_3$)alkylamino, halogen, halogenoalkyl or hydroxyl group, $R_4$ represents a hydrogen atom or a ($C_1$–$C_4$)alkyl, alkylaryl or ($C_1$–$C_6$)alkylamino group, and n assumes values of 0, 1 or 2.

2. A non-toxic, pharmaceutically acceptable salt of a compound as claimed in claim 1, obtained by addition of an acid or alkyl halide.

3. A compound as claimed in claim 1, wherein $R_2$ and $R_3$ are hydrogen, $R_4$ is methyl, n is 1 or 2, and R and $R_1$ are hydrogen, methyl or ethyl.

4. A compound as claimed in claim 3, selected from the group comprising:
 6-methyl-6,11-dihydro-11-(N,N-dimethylamino-acetyl)dibenzo[c,f][1,2,5]thiadiazepine 5,5-dioxide,
 6-methyl-6,11-dihydro-11-[3-(N,N-dimethylamino)-propionyl]-dibenzo[c,f][1,2,5]thiadiazepine 5,5-dioxide,
 6-methyl-6,11-dihydro-11-(N,N-diethylamino-acetyl)dibenzo[c,f][1,2,5]thiadiazepine 5,5-dioxide,
 6-methyl-6,11-dihydro-11-(N-methylamino-acetyl)-dibenzo[c,f][1,2,5-thiadiazepine 5,5-dioxide,
 6,9-dimethyl-6,11-dihydro-11-(N,N-dimethylamino-acetyl)dibenzo[c,f][1,2,5]thiadiazepine 5,5-dioxide,
 8-chloro-6-methyl-6,11-dihydro-11-(N,N-dimethyl-amino-acetyl)dibenzo[c,f][1,2,5]thiadiazepine 5,5-dioxide.

5. A pharmaceutically acceptable acid addition salt of 6-methyl-6,11-dihydro-11-(N,N-dimethylamino-acetyl)-dibenzo[c,f][1,2,5]thiadiazepine 5,5-dioxide.

6. Pharmaceutical composition comprising an active dose for action on the central nervous system for antidepressant action, of at least one compound of claim 1 together with a pharmaceutically acceptable vehicle.

7. Composition of claim 6 in a pharmaceutical form suitable for oral, parenteral or rectal administration.

8. Pharmaceutical composition comprising an effective quantity of a compound acting on the central nervous system by its antidepressant action, selected from the group comprising derivatives of 11-carbonyl-6,11-dihydro-dibenzo[c,f][1,2,5]thiadiazepine 5,5-dioxide of the formula

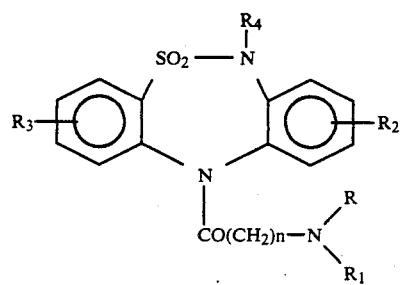

where R, $R_1$, $R_2$, $R_3$, $R_4$ and n have the meaning given for them in claim 1.

9. A pharmaceutical composition comprising an active dose for its action on the central nervous system by antidepressant action, of a compound of claim 4 in a pharmaceutical form suitable for oral, parenteral or rectal administration.

* * * * *